United States Patent [19]

Nakazawa et al.

[11] Patent Number: 5,143,708
[45] Date of Patent: Sep. 1, 1992

[54] TETRACOSAHEDRAL SILICEOUS PARTICLES AND PROCESS FOR PREPARATION THEREOF

[75] Inventors: Tadahisa Nakazawa, Tokyo; Masahide Ogawa, Shibata; Kiyoshi Abe, Shibata; Kazuhiki Suzuki, Shibata; Jun Suzuki, Nakajo, all of Japan

[73] Assignee: Mizusawa Industrial Chemicals, Ltd., Tokyo, Japan

[21] Appl. No.: 175,177

[22] Filed: Mar. 30, 1988

[30] Foreign Application Priority Data

Mar. 31, 1987 [JP] Japan .................................. 62-76395
Mar. 23, 1988 [JP] Japan .................................. 63-67223

[51] Int. Cl.$^5$ ...................... C01B 33/26; C01B 33/12; H01B 3/20
[52] U.S. Cl. .................................. 423/328; 252/572; 252/573; 423/335
[58] Field of Search ............ 423/335, 118, 328, 328.2; 502/85, 408; 252/75, 573, 572

[56] References Cited

U.S. PATENT DOCUMENTS

| | | | |
|---|---|---|---|
| 1,932,832 | 10/1933 | Turrentine ........................ | 502/408 |
| 3,836,561 | 9/1974 | Young .................................. | 502/85 |
| 4,343,723 | 8/1982 | Rogers et al. ..................... | 423/328.2 |
| 4,702,855 | 10/1987 | Goossen et al. ..................... | 252/74 |

FOREIGN PATENT DOCUMENTS

| | | | |
|---|---|---|---|
| 284245 | 5/1929 | United Kingdom ................. | 502/85 |
| 574911 | 1/1946 | United Kingdom ................. | 502/85 |

OTHER PUBLICATIONS

Grant, Hackh's Chemical Dictionary, 4th Ed. McGraw-Hill Book Co. 1969, p. 44.

*Primary Examiner*—Jeffrey E. Russel
*Attorney, Agent, or Firm*—Spensley Horn Jubas & Lubitz

[57] ABSTRACT

Active analcime having a chemical composition comprising 60 to 95% by weight of $SiO_2$, 0.3 to 20% by weight of $Al_2O_3$ and 0.02 to 11% by weight of $Na_2O$ based on the three components, an X-ray diffraction pattern inherent to analcime and a moisture adsorption of 5 to 30% by weight as determined under conditions of a relative humidity of 90%, an ambient temperature of 25° C. and a standing time of 24 hours, wherein individual particles have a tetracosahedral or angle-rounded tetracosahedral particulate shape and the primary particle size of 0.1 to 50 μm as determined according to the electron microscope method. This active analcime is obtained by acid-treating a zeolite by using an acid in an amount of 0.1 to 1.2 molar equivalents per mole of the sum of $Al_2O_3$ and $Na_2O$ components in the zeolite so that the crystal structure of analcime is left.

Amorphous silica which is obtained by an acid treatment of a zeolite and is X-ray diffractometrically substantially amorphous, wherein individual particles have a tetracosahedral or angle-rounded tetracosahedral particulate shape and the primary particle size is 0.1 to 50 μm as determined according to the electron microscope method. This amorphous silica is obtained by acid-treating a zeolite so that $Al_2O_3$ and $Na_2O$ components are removed in amounts sufficient to render the zeolite amorphous.

14 Claims, 4 Drawing Sheets

TETRACOSAHEDRAL SILICEOUS PARTICLES AND PROCESS FOR PREPARATION THEREOF

BACKGROUND OF THE INVENTION

1. Field of the Invention

The present invention relates to amorphous silica and active analcime having a novel particulate shape, and a process for the preparation thereof. More particularly, the present invention relates to a process for preparing active analcime or amorphous silica from an analcime type zeolite.

2. Description of the Prior Art

Synthetic analcime is a known substance, and it is known that this substance can be obtained by subjecting silica, caustic alkali and aluminum hydroxide or an aluminate at a ratio corresponding to the composition of analcime to hydrothermal reaction.

It also is known that synthetic analcime having a sharp particle size distribution is valuably used as a filler for cosmetics, a filler for paints, an antiblocking agent for films, a carrier for liquid chromatography and a spacer for liquid crystals (see, for example, Japanese Patent Application Laid-Open Specification No. 186413/85).

However, synthetic analcime is composed of extremely inactive inorganic particles. For example, the BET specific surface area of synthetic analcime is smaller than 5 $m^2/g$ and the moisture absorption determined under conditions of a relative humidity of 90%, an ambient temperature of 25° C. and a standing time of 48 hours is zero or substantially zero.

There are various application objects of fillers or filling materials used for various products of resins, rubbers, papers, oils, detergents and cosmetics, and in many cases, particles of the fillers or filling materials are required to have at least a certain surface activity. For example, this surface activity is necessary for preventing migration of additives in a resin or rubber or for absorbing an ink in case of paper.

SUMMARY OF THE INVENTION

We found that when synthetic analcime is acid-treated under specific conditions described in detail hereinafter, active analcime having novel characteristics is obtained and when synthetic analcime is drastically acid-treated, amorphous silica retaining a tetracosahedral shape inherent to analcime is obtained.

It is therefore a primary object of the present invention to provide active analcime and a process for the preparation thereof.

Another object of the present invention is to provide active analcime having a specific particulate shape and a specific size and also having a low pH value and characteristics of a solid acid and a process for the preparation thereof.

Still another object of the present invention is to provide active analcime which is thermally stable and is excellent in the effect of improving the electroviscosity and a process for the preparation thereof.

A further object of the present invention is to provide amorphous silica having a fine primary particle size and a novel particulate shape and a process for the preparation thereof.

A still further object of the present invention is to provide amorphous silica which has a good dispersibility in resins and a good compatibility with resins and is capable of preventing formation of voids between resins and particles in various resin processings.

In accordance with one fundamental aspect of the present invention, there is provided a process for the preparation of siliceous particles having a tetracosahedral shape or an angle-rounded tetracosahedral shape, which comprises the step of synthesizing zeolite particles having an X-ray diffraction pattern inherent to analcime, the individual particles having a tetracosahedral shape or an angle-rounded tetracosahedral shape, and the step of acid-treating the zeolite to remove at least parts of $Al_2O_3$ and $NaO_2$ in the zeolite.

In accordance with another aspect of the present invention, there is provided active analcime having a chemical composition comprising 60 to 95% by weight of $SiO_2$, 0.3 to 20% by weight of $Al_2O_3$ and 0.02 to 11% by weight of $Na_2O$ based on the three components, an X-ray diffraction pattern inherent to analcime and a moisture adsorption of 5 to 30% by weight as determined under conditions of a relative humidity of 90%, and ambient temperature of 25° C. and a standing time of 24 hours, wherein individual particles have a tetracosahedral or angle-rounded tetracosahedral particulate shape and the primary particle size is 0.1 to 50 $\mu m$ as determined according to the electron microscope method. This active analcime is obtained by acid-treating a zeolite by using an acid in an amount of 0.1 to 1.2 molar equivalents per mole of the sum of $Al_2O_3$ and $Na_2O$ components in the zeolite so that the crystal structure of analcime is left.

In accordance with still another aspect of the present invention, there is provided amorphous silica which is obtained by an acid treatment of a zeolite and is X-ray diffractometrically substantially amorphous, wherein individual particles have a tetracosahedral or angle-rounded tetracosahedral particulate shape and the primary particle is 0.1 to 50 $\mu m$ as determined according to the electron microscope method. This amorphous silica is obtained by acid-treating a zeolite so that $Al_2O_3$ and $Na_2O$ components are removed in amounts sufficient to render the zeolite amorphous, that is, by using an acid in an amount of at least 1.5 molar equivalents per mole of the sum of $Al_2O_3$ and $Na_2O$ components in the zeolite.

DETAILED DESCRIPTION OF THE PREFERRED EMBODIMENTS

Figure 1:
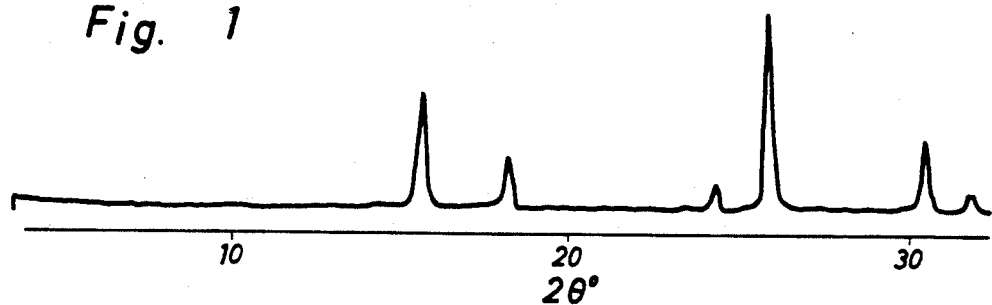
FIG. 1 is an X-ray diffraction pattern of active analcime particles (sample 1-4) according to the present invention.

The present invention will now be described in detail.

Preparation of Analcime Type Zeolite

For the production of active analcime and amorphous silica of the present invention, zeolite particles having an X-ray diffraction pattern inherent to analcime and a definite tetracosahedral or angle-rounded tetracosahedral shape are first prepared.

An analcime type zeolite having such a particulate shape is known. However, according to the conventional synthesis process, it is impossible to synthesize only an analcime type zeolite having the above-mentioned particulate shape and a good dispersibility.

According to the present invention, an analcime type zeolite is synthesized by mixing sodium silicate or active silica gel, sodium aluminate and sodium hydroxide so that conditions described below are satisfied, to form an alkali metal aluminosilicate gel, homogenizing the gel and crystallizing the gel at a temperature of 80° to 200° C. under atmospheric pressure or under hydrothermal reaction conditions.

| Component Ratio | Molar Ratio | Preferred Molar Ratio |
| --- | --- | --- |
| $Na_2O/SiO_2$ | 0.5 to 5.0 | 0.7 to 3.0 |
| $SiO_2/Al_2O_3$ | 3 to 50 | 5 to 20 |
| $H_2O/Na_2O$ | 20 to 500 | 50 to 200 |

The formed zeolite is washed with water and is then sieved to obtain particles having a predetermined particle size. Then, the following acid treatment is carried out.

According to the present invention, active analcime is prepared by using the so-synthesized analcime type zeolite. A typical chemical composition of this analcime type zeolite is as follows.

| Chemical Composition of Analcime Type Zeolite | |
| --- | --- |
| $SiO_2$ | 49 to 59% by weight |
| $Al_2O_3$ | 21 to 25% by weight |
| $Na_2O$ | 12 to 14% by weight |
| $H_2O$ (ignition loss) | 7 to 10% by weight |

Acid Treatment

In accordance with the first aspect of the present invention, the above-mentioned zeolite particles are subjected to an acid treatment to form active analcime. It is preferred that the acid treatment be carried out so that the crystal retention ratio in the product is 1 to 75%, especially 5 to 50%. For this purpose, it is preferred that the acid treatment be carried out by using an acid in an amount of 0.1 to 1.2 molar equivalents, especially 0.3 to 1.0 molar equivalent, per mole of the $Al_2O_3$ and $Na_2O$ components in the zeolite.

The acid used for the acid treatment is not particularly critical and either an inorganic acid or an organic acid can be used, but from the economical viewpoint, it is preferred that a mineral acid such as hydrochloric acid, sulfuric acid, nitric acid or phosphoric acid be used. The acid is preferably used in the form of an aqueous solution for neutralization of the zeolite or elution of the alumina component.

For the acid treatment, the crystalline zeolite is preferably formed into an aqueous slurry, and the acid is added to the slurry. By addition of the acid, the pH value shifts to the acidic side and a certain pH value is obtained. It is preferred that the acid treatment be carried out at a pH value smaller than 4, especially at a pH value smaller than 2.

With reference to other acid treatment conditions, the temperature is preferably 20° to 100° C., and the concentration of the zeolite particles in the slurry is preferably 5 to 30% by weight.

The acid treatment can be conducted in one stage or a plurality of stages. The acid treatment of the present invention is characterized in that the acid treatment is accomplished in one stage.

As is apparent from the above-mentioned chemical composition, the analcime type zeolite to be subjected to the acid treatment in the present invention is characterized in that the contents of the sodium and alumina components to be removed by the acid treatment, especially the alumina component, are especially low. Therefore, according to the present invention, active analcime can be obtained by the one-stage acid treatment. The reaction time is preferably 0.5 to 5 hours.

The obtained active analcime particles are washed with water, dried, pulverized and sieved if necessary, and then calcined according to the need, whereby a final product is obtained. The surfaces of the obtained particles may be treated with a metal soap, a resin acid soap, a resin, a wax, a silane or titanium type coupling agent or a silica coating agent, if desired.

In accordance with another aspect of the present invention, the above-mentioned analcime type zeolite is drastically acid-treated to form amorphous silica. For the production of amorphous silica, it is necessary to remove the $Al_2O_3$ and $Na_2O$ components contained in the zeolite in amounts sufficient to render the zeolite amorphous by the acid treatment. For this purpose, it is preferred that the acid treatment be carried out by using an acid in an amount of at least 1.3 molar equivalents, especially at least 1.5 molar equivalents, per mole of the sum of the $Al_2O_3$ and $Na_2O$ components in the zeolite. Since the amount used of the acid is large, the pH value reached by the acid treatment is lower than 1, especially lower than 0.5.

Other conditions may be the same as those adopted for the preparation of active analcime. However, in order to promote the removal of the $Al_2O_3$ and $Na_2O$ components, it is preferred that a temperature condition of 50° to 100° C. be adopted. More specifically, there is preferably adopted a method in which the analcime type zeolite is maintained at normal temperature for about 0.5 to about 2 hours, the temperature is elevated to 70° to 100° C. and the zeolite is maintained at this temperature for 70° to 100° C. Also this acid treatment may be carried out in one stage or a plurality of stages. Of course, the formed amorphous silica particles may be subjected to the above-mentioned post treatment.

In general, a plurality of stages of acid treatments are necessary for preparing amorphous silica from zeolite A or the like. Namely, at the first stage of the acid treatment, the sodium component in the zeolite is removed, and the acid-treated product is dried or calcined. By the acid treatment of the second and subsequent stages, the alumina component is eluted and removed. The reason why this multi-staged acid treatment is necessary is that a large quantity of the alumina component, the removal of which is difficult by the acid treatment, is contained in zeolite A or the like and the particles are liable to collapse.

In contrast, in analcime type zeolite to be acid-treated in the present invention, the amounts of the sodium component and the alumina component to be removed by the acid treatment, especially the alumina component, are very small, as is seen from the above-mentioned chemical composition. Accordingly, in the present invention, the sodium component and alumina component can be removed in amounts sufficient to render the zeolite amorphous by the one-stage acid treatment.

In the present invention, the starting zeolite needs not to be particularly dried or calcined at the acid treatment. Namely, in order to prevent the collapse of the particulate shape of the starting zeolite, it is generally necessary to dry or calcine the starting zeolite. On the other hand, since the zeolite particles used in the present invention have a tetracosahedral shape close to a true sphere and are sufficiently satisfactory in the strength, the particulate shape is sufficiently retained even if the drying treatment or the calcination treatment is not carried out. (Active Analcime)

The present invention is characterized in that analcime zeolite, individual particles of which have a tetracosahedral or angle-rounded tetracosahedral shape, is used and these particles are acid-treated within such a range as maintaining the crystallinity to remove parts of the sodium and alumina components, whereby active analcime having an appropriate surface activity is obtained.

Active analcime of the present invention has the following composition (% by weight) based on the three components.

|  | General Range | Preferred Range |
| --- | --- | --- |
| SiO$_2$ | 60 to 95% | 75 to 90% |
| Al$_2$O$_3$ | 0.3 to 20% | 1 to 15% |
| Na$_2$O | 0.02 to 12% | 0.5 to 5% |

In this active analcime, the Al$_2$O$_3$ and Na$_2$O contents are lower than in analcime per se, and the SiO$_2$ content is accordingly increased. This composition has close relations to the crystal form, infrared absorption spectrum, moisture absorption, specific surface area and other properties described hereinafter.

Figure 2:
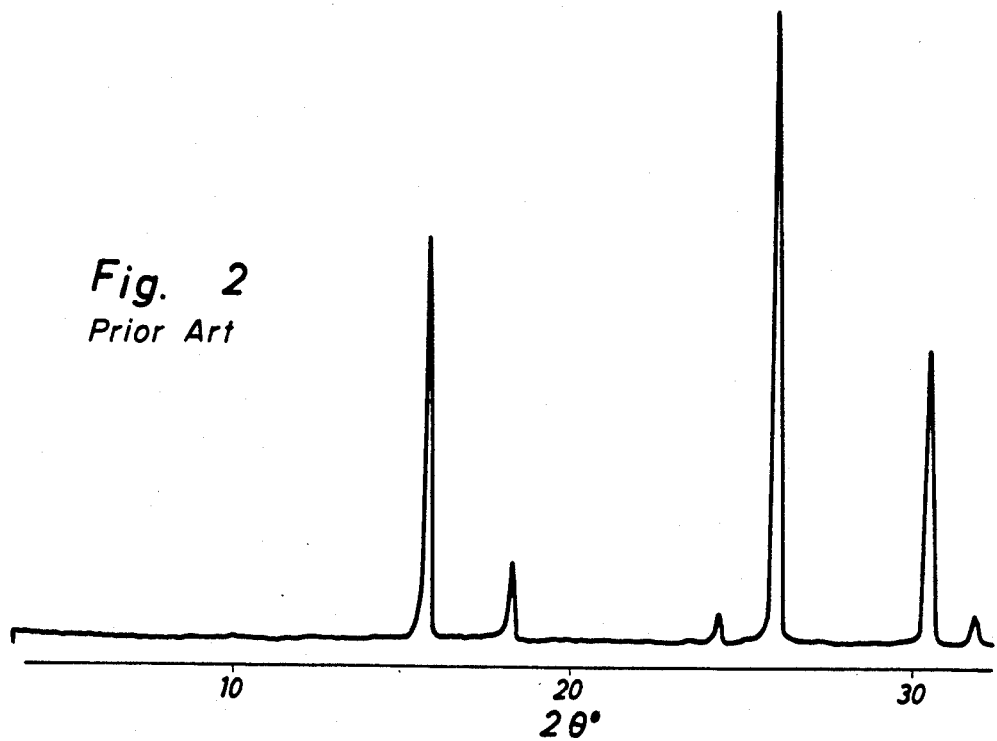
FIG. 2 is an X-ray diffraction diagram of the starting analcime type zeolite (sample 1-0).
Figure 3:
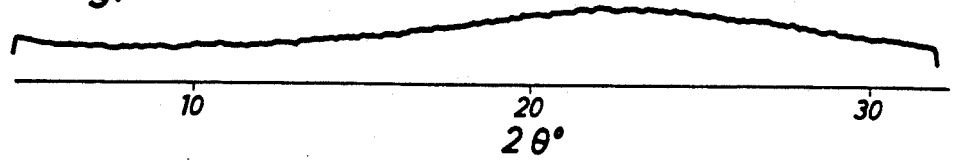
FIG. 3 is an X-ray diffraction diagram of a product (sample 1-7) obtained by drastically acid-treating the starting analcime type zeolite.

In this active analcime, parts of the Al$_2$O$_3$ and Na$_2$O components of analcime are removed, but the active analcime still has an X-ray diffraction pattern inherent to analcime. FIG. 1 of the accompanying drawings shows an X-ray diffraction pattern of the active analcime, FIG. 2 shows an X-ray diffraction pattern of the starting analcime, and FIG. 3 shows an X-ray diffraction pattern of amorphous silica obtained by drastically acid-treating the starting analcime. From these FIGS., it is seen that the active analcime has the X-ray diffraction pattern inherent to the starting analcime, though the peak heights are reduced.

The active analcime of the present invention has a crystal retention ratio of 1.0 to 75%, especially 5 to 50%, as determined according to the method described hereinafter. If the crystal retention ratio is too low and below the above-mentioned range, the characteristics inherent to the analcime type zeolite are lost, and if the crystal retention ratio is too high and exceeds the above-mentioned range, the intended surface activity cannot be obtained.

The degree of the surface activity can be expressed by the moisture absorption or BET specific surface area. The active analcime of the present invention has a moisture absorption of 5 to 30%, especially 7 to 20%, as determined under conditions of a relative humidity of 90%, an ambient temperature of 25° C. and a standing time of 24 hours. Furthermore, the active analcime of the present invention has a BET specific surface area of 50 to 500 m$^2$/g, especially 150 to 400 m$^2$/g, though the BET specific surface area changes to some extent according to the particle size. From the fact that the moisture absorption of analcime is smaller than 1% and the BET specific surface area of analcime is smaller than 2 m$^2$/g, it is understood that the active analcime of the present invention has a large surface activity.

Analcime has a chemical structure typically represented by the following formula:

$$Na_{16}[(AlO_2)_{16}(SiO_2)_{32}]\cdot 16H_2O \qquad (1)$$

The crystal system of analcime is cubic, the lattice constant (a) is 13.72 Å, and the pore diameter is 2.6 Å and is smallest among zeolites.

From the foregoing facts, it is considered that the active analcime of the present invention has the following micro-structure. Namely, each of the particles of the active analcime has a structure comprising a core composed of sodium aluminosilicate having an analcime type crystal structure and a dense shell composed of amorphous silica or silica-alumina, which is present around the core. Accordingly, the active analcime particles have a surface activity of adsorbing water in the surface and have a characteristic property of gradually releasing the Na$_2$O contained in the interior.

In fact, even though the active analcime of the present invention has the Na$_2$O component in the above-mentioned amount, an aqueous dispersion of the active analcime is neutral or weakly acidic and a 1% aqueous suspension of the active analcime has a pH value of 4 to 8, especially 5 to 7. This active analcime has characteristics of a solid acid, and the acid amount corresponding to an acid strength function pKa of up to 4.8 is in the range of from 0.2 to 1.0 millimole/g, especially from 0.3 to 0.8 millimole/g.

Figure 5:
FIGS. 5, 6, 7 and 8 are electron microscope photos (10,000 magnifications) of particles of samples 1-4, 1-0, 1-7 and 4-1.
Figure 6:

FIG. 6 of the accompanying drawings is an electron microscope photo (10,000 magnifications) of active analcime of the present invention. FIG. 5 is an electron microscope photo (10,000 magnifications) of analcime type zeolite particles, which is shown for comparison.

From these electron microscope photos, it is understood that the active analcime particles of the present invention, as well as the analcime type zeolite particles, have as a whole a tetracosahedral or angle-rounded tetracosahedral shape close to a true sphere.

Another characteristic of the active analcime of the present invention is that although the respective particles have a definite particulate shape as described above, a relatively small particle size is maintained, that is, the primary particle size is 0.1 to 50 μm, especially 0.3 to 30 μm.

If the primary particle size is too small and below the above-mentioned range, agglomeration is often caused and such a small primary particle size is not preferred. If the primary particle size is too large and exceeds the above-mentioned range, the active analcime is not preferable as a resin filler or other additive.

Figure 4:
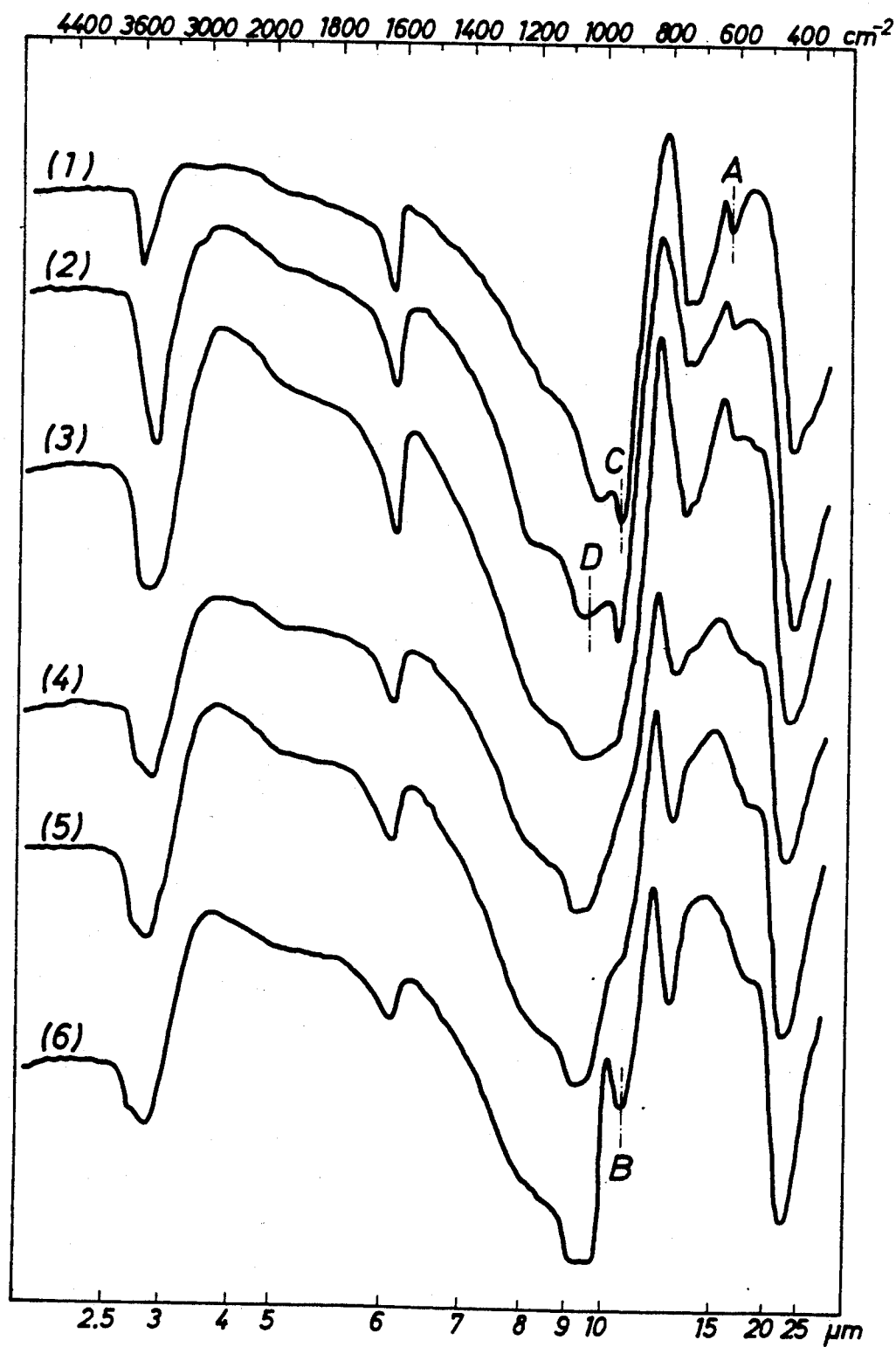
FIG. 4 shows infrared absorption spectrograms of particles of starting analcime (1), active analcimes (2) through (5) and amorphous silica (6), in which A represents the peak at 615 $cm^{-1}$, B represents the peak at 900 $cm^{-1}$, C represents the peak at 950 $cm^{-1}$ and D represents the peak at 1000 to 1130 $cm^{-1}$.

FIG. 4 shows infrared absorption (IR) spectra of the starting analcime and products obtained by acid-treating the starting analcime with various amounts of the acid. From these IR spectra, it is understood that the starting analcime has a peak (C) attributed to the stretching vibration of Si(Al)O at a wave number of about 950 cm$^{-1}$ but this peak shifts to a wave number of 1000 to 1130 cm$^{-1}$ as the result of the acid treatment. It also is understood that the starting analcime has a characteristic peak attributed to the analcime crystal at a wave number of about 610 cm$^{-1}$ and this peak is reduced as the degree of the acid treatment increases.

Since the active analcime of the present invention has a tetracosahedral or angle-rounded tetracosahedral particulate shape close to a true sphere, the active analcime of the present invention has characteristics of spherical particles, that is, a good flowability of particles, a large bulk density and an excellent dispersibility in a resin or the like.

The fact that the particulate shape of the active analcime of the present invention is not a shape of a true sphere but is substantially polyhedral has great influences on the interfacial characteristics of the active analcime particles to other substances.

For example, when the particles of the present invention are incorporated into a resin and the composition is molded, since the particle surfaces are in gear with the resin, even if the formed film is subjected to drawing or the like, formation of voids is controlled and an excellent film in which fish eyes are hardly observed and the transparency is high is obtained.

Furthermore, since the active analcime of the present invention has the above-mentioned definite particulate shape, the individual particles hardly agglomerate and the active analcime of the present invention can have a sharp particle size distribution.

According to the intended use, the active analcime of the present invention can be used either in the state where the primary particle size is uniform and the particle size distribution is sharp or in the state where the primary particle size has a broad distribution. In the former case, the particles can have a standard deviation ($\sigma$) of the primary particle size smaller than 0.85, especially smaller than 0.5.

Since the active analcime of the present invention has the above-mentioned particulate shape, particle size characteristics, surface activity and appropriate pH value, the active analcime of the present invention can be used as a filler, a filling material or other additive for various products.

For example, the active analcime of the present invention is incorporated in various resins, for instance, olefin resins such as polypropylene, polyethylene, a crystalline propylene/ethylene copolymer, an ion-crosslinked olefin copolymer and an ethylene/vinyl acetate copolymer, thermoplastic polyesters such as polyethylene terephthalate and polybutylene terephthalate, polyamides such as 6-nylon and 6,6-nylon, chlorine-containing resins such as a vinyl chloride resin and a vinylidene chloride resin, polycarbonates, polysulfones, and thermoplastic resins such as polyacetal, and the active analcime is used for imparting a slipping property or anti-blocking property to molded products of these resins, such as biaxially drawn films.

In this application, the amount incorporated of the active analcime varies according to the intended use, but it is preferred that the active analcime be incorporated in an amount of 0.01 to 5% by weight, especially 0.05 to 1% by weight, based on the resin.

Moreover, the active analcime of the present invention can be used as a filler or reinforcer for a molding thermosetting resin or a coating-forming paint, or as a ceramic substrate.

The particles of the active analcime of the present invention are different from ordinary zeolite particles in that they show a neutral or weakly acidic pH value and dilution of Na$^+$, Al$^{+3}$ or the like is not caused. Accordingly, the active analcime of the present invention is valuable as a base of various cosmetics such as powder foundation, liquid (pasty) foundation, baby powder and cream, or as a carrier for supporting a medicine, an agricultural chemical, a perfume or an aromatic agent. Moreover, the active analcime can be used as a carrier in various chromatographies.

The active analcime shows an alternating current conduction of less than 0.1 mA as determined according to the method described below, and this alternating current conduction is maintained for a long electrification time. Since each of the starting analcime and the amorphous product obtained by drastically acid-treating the starting analcime has a larger alternating current conduction and a silica or silica-alumina gel heretofore used for an electroviscous fluid is poor in the durability of the electric conductivity, it is deemed that the above-mentioned micro-structure of active analcime has a close relation to the fact that the active analcime is excellent in the durability of the electroconductivity, though the electroconductivity is relatively small. The active analcime of the present invention can be incorporated into an oil such as an organopolysiloxane in an amount of 10 to 70% by weight based on the oil to form an electroviscous fluid.

Amorphous Silica

In accordance with still another aspect of the present invention, amorphous silica particles are obtained by acid-treating analcime type zeolite particles, each having a tetracosahedral or angle-rounded tetracosahedral shape, to remove the sodium component and alumina component.

The amorphous silica of the present invention prepared by using the above-mentioned analcime type zeolite particles has a definite particulate shape as the zeolite particles, and the particle size of the amorphous silica is very fine.

Figure 7:
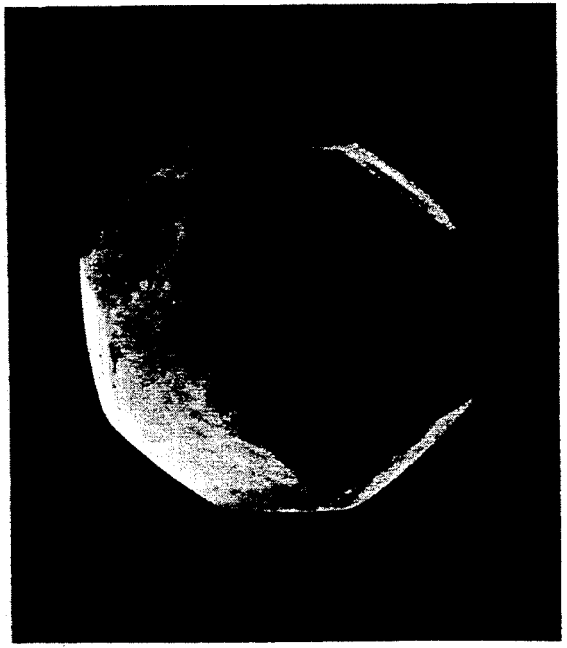

FIG. 7 of the accompanying drawings is an electron microscope photo (10,000 magnifications) of the amorphous silica particles of the present invention, and FIG. 5 is an electron microscope photo (10,000 magnifications) of the analcime type zeolite particles, which is shown for comparison.

From these electron microscope photos, it is understood that the amorphous silica particles of the present invention, as well as the analcime type zeolite particles, have as a whole a tetracohedral or angle-rounded tetracosahedral shape close to a true sphere.

FIG. 3 shows an X-ray diffraction pattern (Cu-$\alpha$ of the amorphous silica particles and FIG. 2 shows an X-ray diffraction pattern of the analcime type zeolite particles. From the infrared spectra shown in FIG. 4, it is seen that the product obtained by the drastic acid treatment has a peak B attributed to amorphous silica at a wave number of about 900 cm$^{-1}$ as in curve (6). From the X-ray diffraction patterns shown in FIGS. 2 and 3, it is seen that the product of the present invention has a particulate structure similar to that of the analcime type zeolite particles. However, the product of the present invention is different from the analcime type zeolite particles in that the product of the present invention is amorphous from the viewpoint of either the X-ray diffractiometry or the infrared absorption spectroscopy.

Another characteristic of the amorphous silica of the present invention is that although respective particles have the above-mentioned definite particulate shape, the primary particle size is relatively small and in the range of from 0.1 to 50 μm, especially from 0.3 to 30 μm.

If the primary particle size is too small and below the above-mentioned range, secondary agglomeration is often caused, and hence, such a small primary particle size is not preferred. If the primary particle size is too large and exceeds the above-mentioned range, the amorphous silica is not preferably used as a resin filler or the like.

The amorphous silica of the present invention generally has the following composition, though the composition varies to some extent according to the preparation conditions.

| Composition of Amorphous Silica | |
| --- | --- |
| $SiO_2$ | 84 to 99.9% by weight |
| $Al_2O_3$ | 0 to 4% by weight |
| $Na_2O$ | 0 to 0.02% by weight |
| ignition loss | lower than 15% by weight |

Since this amorphous silica has a tetracosahedral or angle-rounded tetracosahedral particulate shape close to a true sphere, the amorphous silica has characteristics of spherical particles, that is, a good flowability of particles, a large bulk density and an excellent dispersibility in a resin or the like.

The fact that the particulate shape of the amorphous silica of the present invention is not a shape of a true sphere but is substantially polyhedral has great influences on the interfacial characteristics of the amorphous silica particles to other substances.

For example, when the particles of the present invention are incorporated into a resin and the composition is molded, since the article surfaces are in gear with the resin, even if the formed film is subjected to drawing or the like, formation of voids is controlled and an excellent film in which fish eyes are hardly observed and the transparency is high is obtained.

Furthermore, since the amorphous silica of the present invention has the above-mentioned definite particulate shape, the individual particles hardly agglomerate and the amorphous silica of the present invention can have a sharp particle size distribution.

According to the intended use, the amorphous silica of the present invention can be used either in the state where the primary particle size is uniform and the particle size distribution is sharp or in the state where the primary particle size has a broad distribution. In the former case, the particles can have a standard deviation ($\sigma$) of the particle size smaller than 0.85, especially smaller than 0.5.

The amorphous silica of the present invention has a BET specific surface area of 200 to 600 $m^2/g$, especially 300 to 500 $m^2/g$. This amorphous silica has a moisture absorption smaller than that of the active analcime, and the moisture absorption is in the range of from 3 to 10%, especially from 4 to 8%.

This amorphous silica can be applied to uses as described above with respect to the active analcime.

The present invention will now be described in detail with reference to the following examples that by no means limit the scope of the invention.

REFERENTIAL EXAMPLE 1

By using commercially available water glass of the reagent class (sodium silicate No. 3, $SiO_2=27\%$ by weight, $Na_2O=9.0\%$ by weight), sodium aluminate ($Al_2O_3=22.5\%$ by weight, $Na_2O=15.5\%$ by weight) and caustic soda, 10 kg of a dilute solution of sodium silicate and 10 kg of a dilute solution of sodium aluminate were prepared.

Then, in a stainless steel vessel having an inner volume of about 18 l, 5 kg of the dilute solution of sodium silicate was gradually mixed with 5 kg of the dilute solution of sodium aluminate with stirring to form an alkali alumino-silicate gel homogeneous as a whole, which had the following composition I or II (molar ratio).

| | I | II |
| --- | --- | --- |
| $Na_2O/SiO_2$ | 1.0 | 1.0 |
| $SiO_2/Al_2O_3$ | 10 | 5.0 |
| $H_2O/Na_2O$ | 70 | 80 |

This alkali aluminosilicate gel was charged in a stainless steel small pressure vessel having an inner volume of 10 l, and the temperature was gradually elevated and crystallization was conducted at 160° C. over a period of 5 hours.

The solid was separated from the mother liquid by suction filtration and was sufficiently washed with water. The obtained analcime type zeolite cake was dried at 110° C. for 24 hours to obtain a starting analcime (sample 1-0-I or 1-0-II). The X-ray-diffraction pattern of sample 1-0-I is shown in FIG. 2 and the electron microscope photo of particles of sample 1-0-I is shown in FIG. 5. The properties of samples 1-0-I and 1-0-II are shown in Table 2.

REFERENTIAL EXAMPLE 2

An angle-rounded tetracosahedral analcime type zeolite (sample 2-0) having a particle size of about 3 μm was prepared in the same manner as described in Referential Example 1 except that a silicic acid gel of fine particles obtained by acid-treating an acid clay produced at Nakajo, Niigata Prefecture, Japan, which is a clay mineral of the smectite group, was used as the starting silicic acid component.

The properties of sample 2-0 are shown in Table 2.

REFERENTIAL EXAMPLE 3

An alkali aluminosilicate having a molar composition of $Na_2O/SiO_2=1.3$, $SiO_2/Al_2O_3=6.0$ and $H_2O/Na_2O=70$ was prepared in the same manner as described in Referential Example 1 by using sodium metasilicate ($Na_2SiO_3\ 9H_2O$) of the reagent class and sodium aluminate. Dry analcime type zeolite particles (sample 3-0) having a particle size of about 25 to 30 μm were prepared from this gel in the same manner as described in Referential Example 1. The properties of the obtained particles are shown in Table 4.

REFERENTIAL EXAMPLE 4

In a stainless steel vessel having an inner volume of 18 l, 5 kg of a dilute solution of commercially available water glass ($SiO_2=10\%$ by weight, $Na_2O=3.2\%$ by weight) was gradually mixed with 5 kg of a dilute solution ($Al_2O_3 = 3.5\%$ by weight, $Na_2O = 3.7\%$ by weight) formed by adding a solution of caustic soda to commercially available sodium aluminate with stirring to form an alkali aluminosilicate gel homogeneous as a whole, which had a molar composition of $SiO_2/Na_2O = 1.50$, $SiO_2/Al_2O_3 = 7.0$ and $H_2O/Na_2O = 90$.

Then, the alkali aluminosilicate gel was charged into a stainless steel small pressure vessel having an inner volume of 10 l, and an analcime type zeolite (sample 4-0) was prepared from this gel in the same manner as described in Referential Example 1. The properties of sample 4-0 are shown in Table 5.

EXAMPLE 1

A beaker having a capacity of 1 liter was charged with 80 g of sample 1-0-I or 1-0-II obtained in Referential Example 1, and 400 ml of pure water was added thereto and the powder was sufficiently dispersed by a magnetic stirrer. Then, a 10% aqueous dilution of hydrochloric acid of the special class was gradually poured at room temperature to the dispersion so that the amount of the acid was 0.2, 0.4, 0.6, 0.8, 1.0 or 1.2 molar equivalents per mole of the $Al_2O_3$ and $Na_2O$ components in the powder of sample 1-0-I or 1.4 molar equivalents per mole of the $Al_2O_3$ and $Na_2O$ components in the powder of sample 1-0-II. Then, the mixture was stirred for 30 minutes.

Then, the temperature was gradually elevated in a water bath and the mixture was maintained at 92° to 95° C. for 5 hours. The solid was separated from the mother liquid by suction filtration, sufficiently washed with water in an amount 10 times by volume the amount of the mother liquid, dried for 24 hours in an electric thermostat drier at 110° C. and pulverized by a small atomizer to obtain active analcime particles. Samples obtained by acid-treating sample 1-0-I with the acid in amounts of 0.2, 0.4, 0.6, 0.8, 1.0 and 1.2 molar equivalents are designated as samples 1-1, 1-2, 1-3, 1-4, 1-5 and 1-6, respectively, and the sample obtained by acid-treating sample 1-0-II with the acid in an amount of 1.4 molar equivalents is designated as sample 1-7 (amorphous silica).

In order to examine the eluting property of the obtained active analcime, 2 g of sample 1-0-I, sample 1-2, sample 1-4 or 1-6 was charged in a beaker having a volume of 500 ml and 300 ml of pure water was added thereto, and the mixture was stirred at 80° C. for 5 hours. The amounts of Al and Na eluted in the solution were determined by the atomic absorption spectroscopy. The obtained results are shown in Table 1. It is seen that in the active analcime according to the present invention, elution of Al and Na is much controlled.

TABLE 1

|  | 1-0-I | 1-2 | 1-4 | 1-6 |
| --- | --- | --- | --- | --- |
| Amount (molar equivalents) of Acid Used for Acid Treatment | 0 | 0.4 | 0.8 | 1.2 |
| Eluted Al (ppm) | 145 | 2.0 | 0.10 | 0.02 |
| Eluted Na (ppm) | 336 | 2.2 | 0.11 | 0.01 |

The infrared absorption (IR) spectra of samples 1-0-I, 1-2, 1-3, 1-4, 1-6 and 1-7 were determined. These IR spectra are shown in FIG. 4 as curves (1) through (6), respectively.

Incidentally, in the present invention, the properties were determined according to the following methods.

(1) Pack Density

The pack density was measured according to the method of JIS K-6220-6-8.

(2) Specific Surface Area

The specific area was measured according to the BET method by using Sorptomatic Series 1800 supplied by Carloelba Co.

(3) Oil Absorption

The oil absorption was measured according to JIS K-5101-19.

(4) Whiteness

The whiteness was measured according to JIS P-8123.

(5) pH Value

The pH value of a 5% aqueous suspension was measured according to JIS K-5101-24A.

(6) Particle Size by Electron Microscope

An appropriate amount of the powdery sample was taken on a metal sample plate and sufficiently dispersed thereon, and a metal was coated by a metal-coating apparatus (Ion Sputter Model E-101 supplied by Hitachi) to form a sample to be photographed. Several electron microscope photographic images differing in the visual field were obtained by using a scanning electron microscope (Model S-570 supplied by Hitachi). Typical particles were selected among spherical particle images in the visual field and the diameter of the spherical particle image was measured as the primary particle size by using a scale.

(7) X-Ray Diffractometry

The sample was passed through a 200-mesh Tyler standard sieve and dried for 5 hours in an electric thermostatic drier at 80° C. Then, the sample was gradually cooled in a desiccator, and the X-ray diffractometry was carried out to identify the crystal form.

Apparatus

X-ray diffraction apparatus supplied by Rigaku Denki, provided with goniometer PMG-S2 and rate meter ECP-D2.

Measurement Conditions

Target: Cu
Filter: Ni
Voltage: 35 kV
Current: 20 mA
Count full scale: $4 \times 10^3$ C/S
Time constant: 1 sec
Chart speed: 1 cm/min
Scanning speed: 1°/min
Diffraction angle: 1°
Slit width: 0.15 mm
Measurement range: $2\theta = 5°$ to 40°

(8) Chemical Composition

The analysis of the ignition loss (Ig-loss), silicon dioxide ($SiO_2$), aluminum oxide ($Al_2O_3$) and sodium oxide ($Na_2O$) was conducted according to JIS M-8852. In the case where the amounts of aluminum oxide and sodium oxide were very small, the atomic absorption spectroscopic method was adopted in combination.

(9) Moisture Absorption

About 1 g of the sample was charged in a weighing bottle of 40 mm × 40 mm, the weight of which had been measured in advance, and the sample was dried for 3 hours in an electric thermostat drier at 150° C. and naturally cooled in a desiccator. The weight of the sample was precisely measured, and the sample was charged in a desiccator having the relative humidity adjusted to 90% by sulfuric acid in advance. After 24 hours, the weight increase was measured as the moisture absorption.

(10) Average Particle Size

A beaker having a capacity of 200 ml was charged with 1 g of the sample, and 150 ml of deionized water was added thereto. The sample was dispersed with stirring for 2 minutes by ultrasonic vibration. The particles of the dispersion were measured by a 50μ aperture tube of Colter Counter (Model TAII). The average particle size was determined from the accumulated distribution diagram.

(11) Acid Strength

The measurement was carried out by the n-butylamine titration method. About 0.5 g of the sample was charged in a 50 ml Erlenmeyer flask having a common plug, and the sample was dried at 150° C. for 3 hours and the weight of the sample was precisely measured. Then, about 10 ml of benzene of the special class dehydrated by distillation was added to the sample. Then, the following Hammett indicator was added to exhibit an acidic color.

| Hammett Indicator | Ho | Acidic Color | Basic Color |
|---|---|---|---|
| Methyl Red | 4.8 | Red | yellow |

The acid strength (the amount of the solid acid) was calculated according to the formula:

$$A = F \times V20 \times W$$

wherein A stands for the amount (millimole/g) of the solid acid, F stands for the factor of N/20 n-butylamine, V stands for the titration amount (ml), and W stands for the weight (g) of the sample.

The termination point of titration was determined based on the hue of "Standard Color Chip" compiled by Japanese Standard Association (based on JIS Z-8721).

(12) Crystal Retention Ratio

The crystal retention ratio (P) was calculated from the sum (Pa) of the peak intensities (mm) of the three strong lines of plane indexes (211), (400) and (332) in the X-ray diffraction pattern of active analcime obtained by acid-treating the analcime crystal according to the following formula:

$$P(\%) = Pa/Po \times 100$$

wherein Po stands for the sum of the peak intensities of the three strong lines of the untreated analcime crystal.

(13) Infrared Absorption Spectrum (IR)

The infrared absorption spectrum was measured by an infrared absorption spectrum apparatus (Model A302 supplied by Nippon Bunko Kogyo).

The properties of the active analcime samples, determined by the above-mentioned methods, are shown in Table 2.

EXAMPLE 2

Active analcime particles (samples 2-1, 2-2 and 2-3) were prepared by acid-treating sample 2-0 obtained in Referential Example 2 with 0.4 to 1.2 molar equivalents of the acid in the same manner as described in Example 1. The properties of these particles determined according to the above-mentioned methods are shown in Table 3.

EXAMPLE 3

Active analcime particles (samples 3-1, 3-2 and 3-3) were prepared by acid-treating sample 3-0 obtained in Referential Example 3 with 0.4 to 1.2 molar equivalents of the acid in the same manner as described in Example 1. The properties of these samples are shown in Table 4.

EXAMPLE 4

Figure 8:
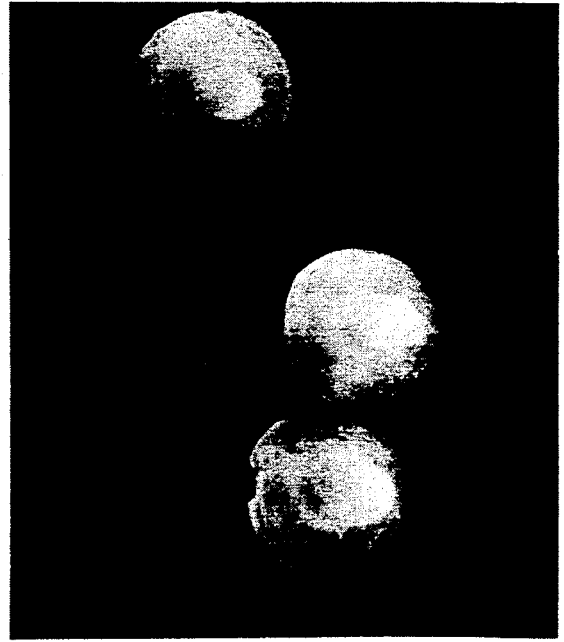
Figure 9:
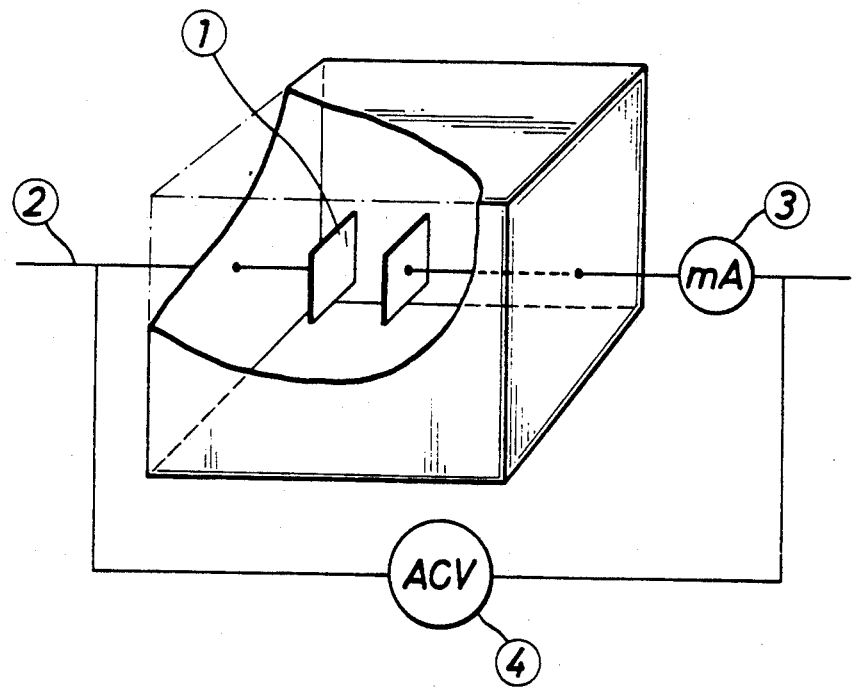
FIG. 9 is a diagram illustrating an experimental apparatus used in Example 6, in which referential numeral 1 represents a stainless steel electrode plate, reference numeral 2 represents a lead line, reference numeral 3 represents an ampere meter and reference numeral 4 represents an alternating current voltage meter.

Amorphous silica (sample 4-1) having a rounded tetracosahedral particulate shape was prepared by acid-treating sample 4-0 obtained in Referential Example 4 with 1.4 molar equivalents of the acid in the same manner as described in Example 1. The properties of the amorphous silica are shown in Table 5. The electron microscope photo of sample 4-1 is shown in FIG. 8.

EXAMPLE 5

A beaker having a capacity of 500 ml was charged with 50 g of amorphous silica particles (sample 4-1) obtained in Example 4, and 300 ml of pure water was added and the particles were sufficiently dispersed in water by a magnetic stirrer. Then, 80 ml of hydrochloric acid (36%) of the reagent class was added to the dispersion, and the mixture was gradually heated and the acid treatment was carried out at 60° C. for 5 hours. After the heat treatment, the reaction mixture was washed with water by decantation, and the abovementioned acid treatment was repeated two times. Filtration, water washing and drying were carried out according to customary procedures to obtain a sample for the micro-analysis (sample 4-2).

The results of the micro-analysis are shown in Table 6.

TABLE 6

| Chemical Composition | Sample 4-2 |
|---|---|
| Ig-loss | 7.41% by weight |
| SiO$_2$ | 92.56% by weight |
| A | 7.6 ppm |
| Na | 3.1 ppm |
| Fe | 2.4 ppm |
| Mg | 2.0 ppm |
| Ca | 1.8 ppm |

EXAMPLE 6

Powder foundation was prepared by using the active analcime of sample 1-4 obtained in Example 1.

| Component (A) | |
|---|---|
| Mica | 38 parts |
| Talc | 12 parts |
| Titanium dioxide | 18 parts |
| Coloring pigment | 4 parts |
| Active analcime | 14 parts |
| Component (B) | |
| Squalane | 5.0 parts |
| Hydrous lanolin | 4.0 parts |
| Isopropyl myristate | 3.0 part |
| Surface active agent | 1.0 part |
| Perfume | appropriate amount |

The predetermined amounts of mica, talc, titanium dioxide, coloring pigment and active analcime of component (A) were charged into a stainless steel vessel, and they were sufficiently mixed and pulverized by an atomizer. Then, the composition was sufficiently mixed by a Henschel mixer, and a heated mixture of the ingredients of component (B) was added to the above composition and the composition was sufficiently mixed to obtain a product.

The comparative test of this foundation and comparative foundation free of the active analcime was performed by randomly selected 20 persons aged from 20 to 50. It was found that the spreading property of the product containing the active analcime was better and this product gave a smooth and neat finish. Furthermore, it was judged that the product gave a good air permeability.

EXAMPLE 7

To 100 parts by weight of a polypropylene resin having a melt flow rate of 1.0 g/10 min were added 0.10 part by weight of 2,6-di-t-butyl-p-cresol, 0.05 part by weight of calcium stearate and 0.2 part by weight of the sample shown in Table 7, and the composition was mixed by a super mixer and pelletized at 230° C. Furthermore, compositions formed by adding synthetic silica (Syloid® 244) or calcium carbonate (Escalon #1500) instead of the sample and the composition to which the sample was not added were similarly pelletized.

Each pelletized product was formed into a sheetlike film by using an extruder, and the film was biaxially drawn at a draw ratio of 6 in each direction to obtain a drawn film having a thickness of 25 μm.

With respect to each of the so-obtained biaxially drawn films, the transparency, blocking property and fish eye property were determined according to the following methods. The obtained results are shown in Table 7.

(1) Transparency

The transparency was determined according to the method of ASTM D-1003.

(2) Blocking Property

Two films were piled and were allowed to stand still under a load of 20 kg in an oven at 40° C. for 24 hours. The force necessary for peeling the two films was measured as the blocking property.

(3) Fish Eye Property

The number of fish eyes having a size larger than 0.1 mm, which were present in an area of 400 cm² of the film, was counted by using an optical microscope.

EXAMPLE 8

Active analcime particles of sample 3-3 obtained in Example 3 were reacted with an n-paraffin having 18 carbon atoms to obtain a sample of a filler for the high-speed liquid chromatography. The comparative test was carried out by using this sample and a commercially available silica type filler.

A column having an inner diameter of 7.8 mm and a length of 30 cm, which was formed of SUS 316 stainless steel, was set at a column filling apparatus. A slurry of the sample in n-hexane was packed in the column under a pressure of 400 kg/cm². The column packed with the active analcime was tested by using a column having the same size and being formed of the same material, as described above, which was packed with a commercially available silica type filler, as the reference column.

A high-speed liquid chromatograph (Waters 6000A) was used for the chromatography. The column temperature was 35° C. and the column pressure was 180 psi. Tetrahydrofuran (THF) was used as the moving phase, and the flow rate of the moving phase was adjusted to 1.0 ml/min. A differential refractive index detector was used as the detector. Under the above-mentioned conditions, a 0.1% solution of polystyrene in tetrahydrofuran was poured into the two columns by using microsyringes. The results obtained in case of the column packed with the active analcime of the present invention were not substantially different from the results obtained in case of the reference column.

EXAMPLE 9

Viscosity characteristics of slurries obtained by dispersing in an organic medium fine particles of the active analcimes of samples 1-4, 1-5 and 2-2 prepared in Examples 1 and 2 were examined according to the following method.

A resin vessel of 5 cm×5 cm×5 cm (see FIG. 6 of the accompanying drawings), in which stainless steel electrode plates having a sectional area of 1 cm² were fixed so that the space between them was 1.5 mm, was used. A silicone oil slurry formed by dispersing the active analcime particles homogeneously in a silicone oil (KF-96 supplied by Shinetsu Kagaku Kogyo) was charged in the vessel to a level of the top ends of the electrode plates. While the slurry was stirred at an elevated temperature of 400° C. by a magnetic stirrer, an alternating current voltage of 2000 V was applied between the electrode plates. The value of the electric current flowing in the slurry was measured, and the degree of solidification of the slurry was evaluated with the naked eye according to a scale described below.

Furthermore, the application of the above-mentioned voltage was repeatedly effected and stopped at intervals of 30 minutes. The restoration of the flowability or solidification with the lapse of time was examined. The obtained results are shown in Table 8. Incidentally, in order to clarify the characteristics of the active analcime particles of the present invention, comparative particles shown in Table 8 were similarly tested.

The scale for the naked eye evaluation of the degree of solidification is as follows.

○: the slurry was sufficiently solidified and did not flow between the electrode plates △: solidification was insufficient and the slurry flow between the electrode plates X: the slurry was not solidified at all

TABLE 2

| | Sample | | | | | | | | |
|---|---|---|---|---|---|---|---|---|---|
| | 1-0-I | 1-0-II | 1-1 | 1-2 | 1-3 | 1-4 | 1-5 | 1-6 | 1-7 |
| Amount (molar equivalents) of acid used for acid treatment | 0 | 0 | 0.2 | 0.4 | 0.6 | 0.8 | 1.0 | 1.2 | 1.4 |
| Pack density (g/ml) | 1.08 | 1.01 | 1.12 | 1.11 | 1.16 | 1.14 | 1.12 | 1.06 | 1.06 |
| Specific surface area (ml/g) | 1.2 | 0 | 68 | 106 | 175 | 274 | 332 | 410 | 390 |
| Oil absorption (ml/100 g) | 28 | 28 | 26 | 25 | 26 | 26 | 27 | 27 | |
| Whiteness (Hunter reflection) (%) | 95 | 95 | 95 | 95 | 95 | 95 | 95 | 95 | |
| pH (25° C.) | 9.2 | 9.2 | 6.8 | 6.1 | 5.5 | 5.5 | 5.3 | 5.4 | 5.1 |
| Particle size (μm) by | 6–7 | 6.5 | 6–7 | 6–7 | 6–7 | 6–7 | 6–7 | 6–7 | 6–7 |

TABLE 2-continued

| | Sample | | | | | | | | |
|---|---|---|---|---|---|---|---|---|---|
| | 1-0-I | 1-0-II | 1-1 | 1-2 | 1-3 | 1-4 | 1-5 | 1-6 | 1-7 |
| electron microscope | | | | | | | | | |
| Crystal retention ratio (%) | 100 | 100 | 63.8 | 42.3 | 23.7 | 13.9 | 6.9 | 2.5 | 0 |
| Absorption (%) (90% RH, 24 hours' standing) | 0.1 | 0 | 6.1 | 7.3 | 9.6 | 13.6 | 17.8 | 20.1 | 6.1 |
| Average particle size ($D_{50}$) (μm) | 7.4 | 7.6 | 7.4 | 7.2 | 7.2 | 7.1 | 7.3 | 7.2 | 7.2 |
| Acid strength (meq/g) | 0.004 | | 0.296 | 0.341 | 0.584 | 0.704 | 0.779 | 0.716 | |
| Chemical composition (% by weight based on product dried at 110° C.) | | | | | | | | | |
| Ig-loss | 7.43 | 7.51 | 6.26 | 8.34 | 7.98 | 8.07 | 8.16 | 7.10 | 7.30 |
| $SiO_2$ | 56.18 | 56.21 | 63.41 | 67.41 | 73.11 | 81.10 | 85.22 | 92.00 | 92.48 |
| $Al_2O_3$ | 23.26 | 23.28 | 19.97 | 15.97 | 12.56 | 7.47 | 4.78 | 0.84 | 0.19 |
| $Na_2O$ | 13.08 | 13.01 | 9.24 | 9.71 | 5.92 | 3.20 | 1.01 | 0.02 | 0.00 |

TABLE 3

| | Sample | | | | |
|---|---|---|---|---|---|
| | 2-0 | 2-1 | 2-2 | 2-3 | 2-4 |
| Amount (molar equivalents) of acid used for acid treatment | 0 | 0.4 | 0.8 | 1.2 | 1.4 |
| Pack density (g/ml) | 0.84 | 0.82 | 0.82 | 0.83 | 0.86 |
| Specific surface area (ml/g) | 1.7 | 120 | 286 | 431 | 411 |
| Oil absorption (ml/100 g) | 34 | 37 | 34 | 35 | |
| Whiteness (Hunter reflection) (%) | 94 | 94 | 94 | 94 | |
| pH (25° C.) | 9.3 | 6.3 | 5.5 | 5.4 | 4.7 |
| Particle size (μm) by electron microscope | 3 | 3 | 3 | 3 | 3 |
| Crystal retention ratio (%) | 100 | 39.1 | 14.1 | 1.9 | 0 |
| Absorption (%) (90% RH, 24 hours' standing) | 0 | 8.5 | 14.7 | 19.8 | 9.3 |
| Average particle size ($D_{50}$) (μm) | 3.6 | 3.4 | 3.5 | 3.4 | 3.5 |
| Acid strength (meq/g) | 0.003 | 0.372 | 0.801 | 0.740 | |
| Chemical composition (% by weight based on product dried at 110° C.) | | | | | |
| Ig-loss | 8.18 | 8.38 | 8.20 | 8.01 | 7.36 |
| $SiO_2$ | 55.14 | 70.22 | 82.25 | 91.32 | 92.50 |
| $Al_2O_3$ | 23.12 | 14.32 | 6.45 | 0.66 | 0.13 |
| $Na_2O$ | 13.53 | 6.76 | 2.96 | 0.02 | 0.00 |

TABLE 4

| | Sample | | | |
|---|---|---|---|---|
| | 3-0 | 3-1 | 3-2 | 3-3 |
| Amount (molar equivalents) of acid used for acid treatment | 0 | 0.4 | 0.8 | 1.2 |
| Pack density (g/ml) | 1.21 | 1.20 | 1.25 | 1.26 |
| Specific surface area (ml/g) | 0 | 79 | 179 | 290 |
| Oil absorption (ml/100 g) | 18 | 18 | 17 | 18 |
| Whiteness (Hunter reflection) (%) | 93 | 94 | 94 | 94 |
| pH (25° C.) | 9.2 | 5.5 | 5.2 | 4.8 |
| Particle size (μm) by electron microscope | 25-30 | 25-30 | 25-30 | 25-30 |
| Crystal retention ratio (%) | 100 | 55.3 | 18.6 | 2.1 |
| Absorption (%) (90% RH, 24 hours' standing) | 0 | 6.9 | 13.0 | 17.1 |
| Average particle size ($D_{50}$) (μm) | 32 | 33 | 32 | 32 |
| Acid strength (meq/g) | 0.002 | 0.203 | 0.681 | 0.543 |
| Chemical composition (% by weight based on product dried at 110° C.) | | | | |
| Ig-loss | 8.34 | 7.91 | 8.27 | 8.00 |
| $SiO_2$ | 55.16 | 66.87 | 90.05 | 90.42 |
| $Al_2O_3$ | 23.04 | 17.12 | 7.90 | 1.28 |
| $Na_2O$ | 13.20 | 7.88 | 3.66 | 0.06 |

TABLE 5

| | Sample | |
|---|---|---|
| | 4-0 | 4-1 |
| Amount (molar equivalents) of acid used for acid treatment | 0 | 1.4 |
| Pack density (g/ml) | 0.89 | 0.93 |
| Specific surface area (ml/g) | 0 | 405 |
| Oil absorption (ml/100 g) | — | — |
| Whiteness (Hunter reflection) (%) | — | — |
| pH (25° C.) | 9.4 | 5.0 |
| Particle size (μm) by electron microscope | 5 | 5 |
| Crystal retention ratio (%) | 100 | 0 |
| Absorption (%) (90% RH, 24 hours' standing) | 0 | 5.2 |
| Average particle size ($D_{50}$) (μm) | 6.4 | 6.3 |
| Acid strength (meq/g) | — | — |
| Chemical composition (% by weight based on product dried at 110° C.) | | |
| Ig-loss | 8.60 | 7.90 |
| $SiO_2$ | 54.17 | 92.00 |
| $Al_2O_3$ | 23.97 | 0.11 |
| $Na_2O$ | 13.24 | 0.000 |

TABLE 7

| Run No. | Additive | | Amount (part by weight) | Transparency (%) | Blocking property (kg/10 cm$^2$) | Number of fish eyes per 400 cm$^2$ |
|---|---|---|---|---|---|---|
| 1 | Sample 2-1 | untreated | 0.20 | 3.3 | 0.24 | 6 |
| 2 | | calcined at 400° C. for 1 hour | 0.20 | 3.5 | 0.20 | 4 |
| 3 | | surface-treated* | 0.20 | 2.8 | 0.22 | 5 |
| 4 | Sample 2-2 | untreated | 0.20 | 3.5 | 0.20 | 6 |
| 5 | | calcined at 400° C. for 1 hour | 0.20 | 3.1 | 0.17 | 3 |
| 6 | | surface-treated* | 0.20 | 2.8 | 0.22 | 7 |
| 7 | Synthetic silica | | 0.20 | 3.5 | 0.25 | 20 |
| 8 | CaCO$_3$ | | 0.20 | 7.2 | 0.60 | 54 |
| 9 | not added | | 0 | 2.0 | 4.0 | — |

Note
*30 g of the sample was thinly spread on a watch glass, 2% of a silane coupling agent (A-1100 supplied by Nippon Unicar; diluted 5 times with ethanol) was sprayed on the sample with stirring by a spatula, and the sample was treated for 3 hours in an electric thermostat drier at 150° C.

TABLE 8

| Run No. | Additive | Amount (% by weight) | Current Quantity (μA) | Degree of solidification (gelation degree) | Durability (days) | Remarks |
|---|---|---|---|---|---|---|
| 1 | Sample 1-4 | 40 | 0.01> | ◯ | 10< | |
| 2 | Sample 1-5 | 40 | 0.01> | ◯ | 10< | |
| 3 | Sample 2-2 | 40 | 0.01> | ◯ | 10< | |
| 4 | Sample 1-5 *1 | 40 | 0.01> | ◯ | 10< | |
| 5 | Sample 1-5 *2 | 40 | 0.01> | ◯ | 10< | |
| 6 | Sample 1-0 | 40 | 5< | ◯ | 5 min> | too large current |
| 7 | Na Zeolite A | 40 | 5< | ◯ | 5 min> | too large current |
| 8 | Na Zeolite X | 40 | 5< | ◯ | 5 min> | too large current |
| 9 | Sample 1-7 | 40 | 0.001> | X | | |
| 10 | Silica gel powder | 30 | 1 | Δ | 1 | |

Note
*1: dispersant (Emsol 20 supplied by Yokohama Kagaku) was added in an amount of 10% based on the silicone oil in the slurry
*2: dispersant (Emsol 20 supplied by Yokohama Kagaku) was added in an amount of 20% based on the silicone oil in the slurry

We claim:

1. Active analcime having a chemical composition comprising 60 to 95% by weight of SiO$_2$, 0.3 to 20% by weight of Al$_2$O$_3$ and 0.02 to 11% by weight of Na$_2$O based on the three components, an X-ray diffraction pattern inherent to analcime and a moisture adsorption of 7 to 30% by weight as determined under conditions of a relative humidity of 90%, an ambient temperature of 25° C. and a standing time of 24 hours, wherein individual particles of the active analcime have a tetracosahedral or angle-rounded tetracosahedral particulate shape and the primary particle size is 0.1 to 50 μm as determined according to the electron microscope method.

2. Active analcime as set forth in claim 1, which has a BET specific surface area of 50 to 500 m$^2$/g.

3. Active analcime as set forth in claim 1, wherein when the active analcime is formed into an aqueous dispersion having a solid concentration of 1%, the pH value is 4 to 8 and the active analcime shows characteristics of a solid acid.

4. Active analcime as set forth in claim 1, wherein the acid amount at an acid strength function of up to 4.8 is 0.2 to 1.0 millimole/g.

5. Active analcime as set forth in claim 1, which has an infrared absorption spectrum having a shifted peak based on stretching vibration of Si(Al)O at a wave number of 1000 to 1130 cm$^{-1}$.

6. Active analcime as set forth in claim 1, wherein the standard deviation (σ) of the primary particle size is smaller than 0.5.

7. An electroviscous fluid comprising active analcime as set forth in claim 1.

8. An electroviscous fluid which comprises an insulating oil and a filler dispersed therein, wherein said filler comprises an active analcime having a chemical composition comprising 60 to 95% by weight of SiO$_2$, 0.3 to 20% by weight of Al$_2$O$_3$ and 0.02 to 11% by weight of Na$_2$O based on the three components, an X-ray diffraction pattern inherent to analcime and a moisture adsorption of 7 to 30% by weight as determined under conditions of a relative humidity of 90%, an ambient temperature of 25° C. and a standing time of 24 hours, wherein individual particles of the active analcime have a tetracosahedral or angle-rounded tetracosahedral particulate shape and the primary particle size is 0.1 to 50 μm as determined according to the electron microscope method, said active analcime being present in an amount of 10 to 70% by weight based on the oil.

9. An electroviscous fluid according to claim 8 wherein the oil comprises an organopolysiloxane oil.

10. Active analcime as set forth in claim 1 wherein the chemical composition comprises 75 to 90% by weight of SiO$_2$, 1 to 15% by weight of Al$_2$O$_3$ and 0.5 to 5% by weight of Na$_2$O based on the three components.

11. Active analcime as set forth in claim 10 wherein the primary particle size is 0.3 to 30 μm.

12. Active analcime as set forth in claim 1 wherein the primary particle size is 0.3 to 30 μm.

13. Active analcime as set forth in claim 1 having a crystal retention ratio of 1.0 to 75%.

14. Active analcime as set forth in claim 1 having a crystal retention ratio of 5 to 50%.

* * * * *